United States Patent [19]

Hayworth

[11] Patent Number: 4,521,352

[45] Date of Patent: Jun. 4, 1985

[54] MICROENCAPSULATION PROCESS

[75] Inventor: Lawrence T. Hayworth, Basingstoke, England

[73] Assignee: Mars, Incorporated, McLean, Va.

[21] Appl. No.: 486,955

[22] PCT Filed: Aug. 9, 1982

[86] PCT No.: PCT/GB82/00249

§ 371 Date: Apr. 6, 1983

§ 102(e) Date: Apr. 6, 1983

[87] PCT Pub. No.: WO83/00449

PCT Pub. Date: Feb. 17, 1983

[30] Foreign Application Priority Data

Aug. 11, 1981 [GB] United Kingdom ................. 8124563

[51] Int. Cl.$^3$ .............................................. B01J 13/02
[52] U.S. Cl. ....................................... 264/4.3; 264/4.7; 424/32; 424/36; 426/805; 428/402.21
[58] Field of Search .............................. 264/4.3, 4.7; 428/402.21

[56] References Cited

U.S. PATENT DOCUMENTS 3,575,882  4/1971  Vandegaer et al. ................. 264/4.7
4,322,311  3/1982  Lim et al. .............................. 264/4.7
4,376,059  3/1983  Davis et al. .......................... 264/4.3

FOREIGN PATENT DOCUMENTS 2026976  2/1980  United Kingdom .
2040863  9/1980  United Kingdom .

OTHER PUBLICATIONS

Handbook of Chemistry and Physics, edited by Hodgman et al., 35th edition, publ. by Chemical Rubber Publ. Co., Cleveland, Ohio, (1953), pp. 912 and 913.

Primary Examiner—Richard D. Lovering
Attorney, Agent, or Firm—Curtis, Morris & Safford

[57] ABSTRACT

In a microencapsulation process involving an interfacial polymerization reaction between a compound containing amine groups and a polybasic acid chloride or anhydride, the polymerization being carried out in an emulsion of an aqueous solution in a hydrophobic organic liquid, the reaction is terminated by introducing water into the hydrophobic phase of the emulsion where it reacts with and destroys the residual acid chloride or anhydride.

11 Claims, No Drawings

MICROENCAPSULATION PROCESS

The present invention relates to microencapsulation processes and more especially to processes for encapsulating fine droplets of a hydrophilic liquid in a hydrophobic continuous phase.

It has been proposed in the prior art to produce microcapsules containing aqueous amine solutions by emulsifying the aqueous solution in an organic liquid with the aid of a suitable surfactant and forming a polymer membrane around the droplets by interfacial polymerisation. For example, it has been proposed to add sebacoyl, succinoyl, adipoyl, phthaloyl, terephthaloyl or citroyl chloride or succinic anhydride to the continuous phase to produce a polyamide membrane. Once the microcapsules have been produced it is frequently desirable to change the continuous phase from a hydrophobic liquid to a hydrophilic liquid, especially water. This is normally effected by decanting or centrifuging off the majority of the hydrophobic liquid, and washing and redispersing the microcapsules several times in a hydrophilic liquid containing large amounts of surfactant.

In the processes proposed in the prior art, certain precautions have to be taken to avoid aggregation of microcapsules, especially at the phase-change stage of the process where the capsules are close together and, for instance, free acid chloride groups in the polymer membrane of one capsule may condense with, for instance, residual free amino groups in the polymer membrane of a second capsule thereby forming chemical bonds between the capsules, or for example, residual acid chloride or anhydride in the reaction medium may condense with residual free amino groups on two or more adjacent capsules.

For many applications of the capsules aggregation or clumping of the capsules is highly undesirable and efforts have been made to ensure that the polymerisation reaction goes to completion thereby avoiding any possibility of aggregation of the capsules.

U.K. Application No. 2040863 discloses a process for the production of microcapsules containing an aqueous solution of a hydrophilic protein containing a plurality of free amine groups, which comprises forming an emulsion of the aqueous protein solution as disperse phase in a substantially non-polar solvent as the continuous phase and adding to the emulsion a solution of a compound containing a plurality of groups capable of reacting with amine groups to form a polymer, especially to form a polyamide.

It is possible when operating in accordance with the instructions of patent specification No. 2040863 to obtain batches of microcapsules in which little or no aggregation has occurred but great care has to be taken in carrying out the process and attempts have therefore been made to find a satisfactory and consistent way of preventing or controlling aggregations of the capsules.

This invention provides a process for microencapsulation of an aqueous amine solution by emulsifying the aqueous solution in an organic liquid and forming a polymer membrane around the droplets by interfacial polymerisation by reaction with a poly basic acid chloride or anhydride, wherein, when the reaction has proceeded to the desired extent the reaction is terminated by introducing water into the reaction medium to react with and destroy residual acid chloride or anhydride.

Water can be introduced into the reaction medium by any method that ensures intimate contact of the water with the acid chloride or anhydride dissolved in the hydrophobic phase of the emulsion or with acid chloride or anhydride groups remaining in the polymer membrane of the capsules.

The water is preferably introduced into the reaction medium by adding to the reaction medium a solution of water in an organic liquid, which solution is substantially miscible with the hydrophobic phase of the emulsion.

The organic liquid serves as a carrier vehicle to introduce water into the hydrophobic phase of the emulsion where it substantially immediately reacts with the acid chloride or anhydride thereby rendering it incapable of taking part in further reaction. Accordingly, when the capsules are brought into close proximity, as for example when the hydrophobic liquid is decanted off, there are no residual acid chloride or anhydride groups available to take part in further reaction with the amine groups.

The organic liquid is preferably a lower aliphatic alcohol containing up to 5 carbon atoms but it may be any liquid that is capable of dissolving water in sufficient quantity to neutralise all the acid chloride or anhydride groups to produce a solution which is miscible with the hydrophobic phase of the emulsion. Preferably, the solvent should dissolve water in an amount of at least 1% and desirably in an amount of at least 3%.

When an alcohol is used as the carrier solvent it has been found in some instances that the walls of the capsules are somewhat stronger than those produced when the reaction is not terminated by the method of the invention and it is thought that this may be due to a certain amount of ester formation by reaction between the alcohol and the free acid chloride or anhydride groups.

Alcohols preferred for use in the process are methanol, ethanol, n-propanol, isopropanol, n-butanol, isobutanol and n-amyl alcohol.

Other liquids that can be used in the process are, for example, the various solvent mixtures that are conventionally used in such operations as fluorometric analysis or assay to introduce water into organic solvents. Among such solvent mixtures there may be mentioned those materials sold under the trade names "Pico-fluor 30" and "Instagel". Pico-fluor 30 is believed to be based on pseudocemene and Instagel is based on a mixture of dioxane and naphthalene.

As an alternative to introducing water in admixture with an organic liquid it is possible to introduce water in admixture with a gas provided that the gas can be introduced into the liquid in sufficiently finely divided form. Moist air can for example be introduced into the liquid through an air stone or through a stirrer having means for the introduction of air.

Following termination of the reaction it has been found that there is no need to use complicated procedures to separate the capsules from the hydrophobic phase. All that is required is to decant off the solvent phase and, for example, to sieve the capsules on a screen. Following this, if desired, the capsules can be dried simply by passing a current of air through the capsules on the screen although other methods such as freeze drying may be used if desired. During this drying process any occluded hydrophobic liquid can be removed from the capsules. Drying may also be carried out to remove the water from within the capsules thereby reducing the density of the capsules. When capsules dried in this way are placed in water they rapidly rehydrate to be ready for use. Following drying of the capsules there may be some caking caused by physical bonding between capsules and this can be broken by agitating the capsules but there is no aggregation of the capsules caused by chemical bonding unless a certain amount of aggregation is desired for some uses of the capsules.

It will be appreciated that since the reaction is terminated substantially immediately it is possible to modify the process of the invention by reducing the volume of the reacting mass so that the capsules are brought closer together to a stage in which a desired degree of aggregation will occur and terminating the reaction at that stage. Thus for example if it is desired to produce clumps of aggregated capsules of a given diameter termination of the polymerisation reaction can be effected to achieve such a goal.

Although the process of the invention is applicable to any microencapsulation process involving an interfacial polymerisation reaction between an amine and an acid chloride or anhydride, the process is particularly applicable to the process described in U.K. patent specification No. 2040863 where the microcapsules are primarily intended for fish food or for carrying pharmaceuticals or the like since it is then possible to ensure that single capsules of the desired size can be obtained in a very simple manner and without extensive precautions against aggregation.

Microcapsules produced by terminating the process of U.K. patent specification No. 2040863 using the process of this invention have all the advantages of the capsules of the earlier application but have various additional advantages. Thus, there is no longer any need to have a specific phase change operation with its repetitive washing operations although some washing may be desirable to remove traces of surfactant; because of the absence of a phase change operation there is little risk of capsule rupture due to changes in osmotic pressure and there is no need to remove any surfactant used in the phase change operation; and because of the reduced chance of aggregation it is possible to reduce the amount of hydrophobic liquid used in the process, the ratio of hydrophobic liquid to aqueous phase can be reduced to as little as 2:1 or even lower.

The following examples illustrate the invention.

In Examples 1 to 6 a diet mix comprising homogenised cod roe, water soluble fish meal, spray dried egg white and glycerol in a ratio of 10:1:1:1 was used.

EXAMPLE 1

13.5 grams of egg lecithin were dissolved in 2,200 mls of cyclohexane while stirring with a high speed stirrer. Stirring was continued while 700 grams of diet were added and the mixture was homogenised by further mixing for 6 minutes to produce an emulsion. 10 mls of succinoyl dichloride in 800 mls of cyclohexane was added and the reaction was allowed to continue for 10 minutes. A solution of 1 gram cholesterol and 4 grams egg lecithin in 210 mls of cyclohexane was then added and stirring was continued for 3 minutes. 200 mls of a 3% solution of water in ethanol was then added and stirring continued for a further 2 minutes. The solvent was decanted off and the capsules were subjected to a freeze drying operation. Good quality dried capsules with no aggregation in a yield of 270 grams were obtained. The dried capsules rehydrated in sea water or fresh water without rupture.

EXAMPLE 2

Example 1 was repeated except that the cholesterol/egg lecithin solution contained 1 gram cholesterol and 2.66 grams of lecithin in 190 mls cyclohexane and was added in an amount of 190 mls.

Similarly good capsules were obtained.

EXAMPLE 3

Example 1 was repeated except that emulsification was stopped after 2 minutes and restarted at faster speed with a smaller bladed rotor.

Similarly good capsules were obtained but they were smaller and less dense than the capsules obtained from Example 1. This is probably due to occluded cyclohexane resulting from the changed emulsification conditions being removed during the freeze drying operation.

EXAMPLE 4

Example 1 was repeated except that the emulsification period was reduced to 5 minutes using a faster speed and a smaller rotor.

Similarly good capsules of a slightly smaller size than those obtained in Example 1 were obtained.

EXAMPLE 5

Example 1 was repeated except that the amount of cyclohexane used in preparing the emulsion was reduced to 1500 mls, the amount of cyclohexane introduced with the acid was reduced to 500 mls and the reaction time was increased to 9 minutes.

Similarly good capsules were obtained.

EXAMPLE 6

1 gram of cholesterol and 4 grams of egg lecithin were dissolved in 2,010 mls of cyclohexane in a 5 liter beaker with stirring using a high speed mixer. 700 grams of diet were added and mixing was continued for 5 minutes to homogenise the mix and form an emulsion. 10 mls of succinoyl chloride in 800 mls of cyclohexane was then added and reaction was continued for 8 minutes. The reaction was terminated by adding 200 mls of a 3% water in ethanol solution and mixing for 2 minutes. The capsules were allowed to settle and the cyclohexane was decanted off. The resulting capsules could be satisfactorily freeze dried and were of the same good quality as those produced in Example 1.

EXAMPLE 7

Example 1 was repeated using 1000 grams of a diet mix consisting of capelin oil, spray dried egg whites and spray dried haemoglobin in water in a ratio of 4:1:1:14. The diet was made up by forming the oil, egg white and haemoglobin into a paste which was then dispersed in the water.

300 grams of good quality capsules were obtained.

EXAMPLE 8

Example 7 was repeated except that in the diet the spray dried hemoglobin was replaced by spray dried whole blood.

Similarly good capsules were obtained.

EXAMPLE 9

Example 1 was repeated using 700 grams of a 20% aqueous solution of bovine haemoglobin.

Good capsules were obtained.

EXAMPLE 10

20 mls of a 6.25% w/w solution of egg lecithin in cyclohexane were added to 200 mls of cyclohexane with stirring and while stirring was continued 70 grams of a 20% w/w solution of egg albumin in water was added. Stirring was continued for 5 minutes to produce an emulsion.

1 ml of succinoyl dichloride dissolved in 80 mls of cyclohexane was added and stirring was continued for a further 5 minutes.

20 mls of n-butanol containing 0.4 mls of water were then added and after a further 2 minutes stirring the solvent was decanted off and the capsules were subjected to a freeze drying operation.

Good quality dried capsules were obtained, the capsules being rehydratable in sea water or fresh water without rupture.

EXAMPLE 11

Example 10 was repeated using 20 mls of isopropanol containing 0.2 mls of water in place of n-butanol. Similar results were achieved.

EXAMPLE 12

Example 10 was repeated using 20 mls of n-propanol containing 0.6 mls of water in place of n-butanol. Similarly good results were obtained.

EXAMPLE 13

Example 10 was repeated using 20 mls of n-amyl alcohol containing 0.2 mls of water in place of n-butanol. Similarly good results were obtained.

EXAMPLE 14

Example 10 was repeated using 20 mls of ethanol containing 0.6 mls of water in place of n-butanol. Similarly good results were obtained.

EXAMPLE 15

Example 10 was repeated except that 0.6 mls of water in 20 mls of Pico-fluor 30 was used in place of the water in butanol solution.

Good capsules were obtained.

EXAMPLE 16

Example 10 was repeated except that instead of pure egg albumin there was used a mixture of egg albumin and bovine hemoglobin in a ratio of 1:1. In addition instead of the solution of water in butanol there was used a solution of 0.6 mls of water in 20 mls of Instagel. Good quality capsules were obtained.

I claim:

1. A process for microencapsulating an aqueous amine solution, which process comprises emulsifying the aqueous amine solution in a hydrophobic organic liquid to form droplets, reacting the amine with a polybasic acid chloride or anhydride to form a polymer membrane around individual droplets by interfacial polymerization, and then terminating the polymerization reaction by introducing water into the hydrophobic organic liquid by adding to the reaction mixture a solution of water in an organic liquid, which solution of water is wholly miscible with the hydrophobic organic liquid.

2. A process according to claim 1 wherein the organic liquid in which water is dissolved is an aliphatic alcohol containing up to 5 carbon atoms.

3. A process according to claim 2, wherein the alcohol is methanol, ethanol, n-propanol, isopropanol, n-butanol, butan-2-ol, or n-amyl alcohol.

4. A process according to claim 2, wherein the reaction is terminated by addition of an approximately 3% solution of water in ethanol.

5. A process according to claim 2, wherein the aqueous amine solution is an aqueous solution of hydrophilic protein containing a plurality of free amine groups.

6. A process according to claim 5, wherein the aqueous amine solution is emulsified in an organic liquid comprising a substantially non-polar solvent.

7. A process as in claim 1 wherein said amine is a protein.

8. A process as in claim 1 wherein said hydrophobic organic liquid is cyclohexane and said solution of water in an organic liquid is a solution of water in ethanol.

9. A process according to claim 1, wherein the acid chloride or anhydride is sebacoyl chloride, succinoyl chloride, adipoyl chloride, phthaloyl chloride, terephthaloyl chloride or citroyl chloride or succinic anhydride.

10. A process according to claim 1, wherein following termination of the reaction the solvent phase is decanted off the capsules.

11. A process according to claim 10, wherein following separation of the capsules from the solvent phase the capsules are dried.

* * * * *